(12) United States Patent
Bourget et al.

(10) Patent No.: US 6,982,334 B2
(45) Date of Patent: Jan. 3, 2006

(54) CRYSTALLINE FORM OF (3R,4R)-4-[3-(S)-HYDROXY-3-(6-METHOXYQUINOLIN-4-YL)PROPYL]-1-[2-(2-THIENYLTHIO) ETHYL]PIPERINDINE-3-CARBOXYLIC ACID

(75) Inventors: Jacques Bourget, Vitry sur Seine (FR); Marc Antoine Perrin, Jouy en Josas (FR); Serge Mignani, Chatenay Malabry (FR); Bernd Janocha, Wiesbaden (DE); Michel Cheve, Soisy sur Seine (FR); Carole Neves, Paris (FR); Pascal Billot, Montreuil (FR); Michel Tabart, La Novrille (FR); Sylvaine Lafont, Trevoux (FR)

(73) Assignee: Aventis Pharma S.A., Antony (FR)

( * ) Notice: Subject to any disclaimer, the term of this patent is extended or adjusted under 35 U.S.C. 154(b) by 42 days.

(21) Appl. No.: 10/739,700

(22) Filed: Dec. 18, 2003

(65) Prior Publication Data

US 2004/0147751 A1    Jul. 29, 2004

Related U.S. Application Data

(60) Provisional application No. 60/480,412, filed on Jun. 20, 2003.

(30) Foreign Application Priority Data

Dec. 20, 2002    (FR) .................................. 02 16415

(51) Int. Cl.
C07D 409/14    (2006.01)
C07D 215/20    (2006.01)
A61K 31/4709    (2006.01)
A61P 31/04    (2006.01)

(52) U.S. Cl. ...................... 546/174; 514/314; 514/311; 546/177; 546/178; 546/180

(58) Field of Classification Search ................ 546/174; 514/314

See application file for complete search history.

(56) References Cited

U.S. PATENT DOCUMENTS 6,403,610 B1    6/2002    Malleron

2004/0147554 A1    7/2004    Bourget

OTHER PUBLICATIONS

Rouhi AM. Chemical & Engineering News, Feb. 2003, pp. 32-34.*
Untitled, Rompp Lexikon Chemie, Georg Thierne Verlag, Stuttgart XP002245011, pp. 3976-3977.
Untitled, Rompp Lexikon Chemie, Georg Thierne Verlag, Stuttgart XP002245011, pp. 2275-2276.

* cited by examiner

Primary Examiner—Evelyn Mei Huang
(74) Attorney, Agent, or Firm—Balaram Gupta

(57) ABSTRACT

The present invention comprises crystalline forms of 3R,4R)-4-[3-(S)-hydroxy-3-(6-methoxyquinolin-4-yl)propyl]-1-[ 2-(2-thienylthio)ethyl]piperidine-3-carboxylic acid, represented by the structure:

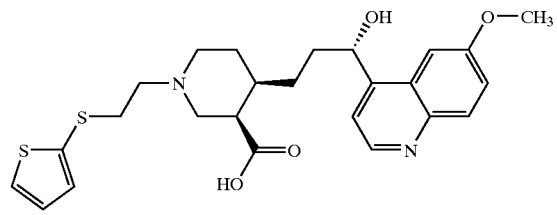

and as characterized herein by powder X-ray diffraction patterns as form A and form B, processes for preparing form A from the purified amorphous form of (3R,4R)-4-[3-(S)-hydroxy-3-(6-methoxyquinolin-4-yl)propyl]-1-[ 2-(2-thienylthio)ethyl]piperidine-3-carboxylic acid, a processes for preparing form A by heating monohydrated form C of (3R,4R)-4-[3-(S)-hydroxy-3-(6-methoxyquinolin-4-yl)propyl]-1-[ 2-(2-thienylthio)ethyl]piperidine-3-carboxylic acid, a pharmaceutical composition comprising form A, a pharmaceutical composition comprising form A and form B or monohydrated form C, a pharmaceutical composition comprising form A, form B and monohydrated form C, a method for treating a bacterial infection with form A, a method for treating a bacterial infection with form A and form B or monohydrated form C, and a method for treating a bacterial infection with form A and form B and monohydrated form C.

4 Claims, No Drawings

CRYSTALLINE FORM OF (3R,4R)-4-[3-(S)-HYDROXY-3-(6-METHOXYQUINOLIN-4-YL)PROPYL]-1-[2-(2-THIENYLTHIO)ETHYL]PIPERINDINE-3-CARBOXYLIC ACID

This application claims priority from French patent application number 0216415, filed Dec. 20, 2002, and the benefit of U.S. Provisional Application No. 60/480,412, filed Jun. 20, 2003.

BACKGROUND OF THE INVENTION

1. Field of the Invention

The present invention relates to a crystalline form of (3R,4R)-4-[3-(S)-hydroxy-3-(6-methoxyquinolin-4-yl)propyl]-1-[2-(2-thienylthio)ethyl]piperidine-3-carboxylic acid, represented by the structure:

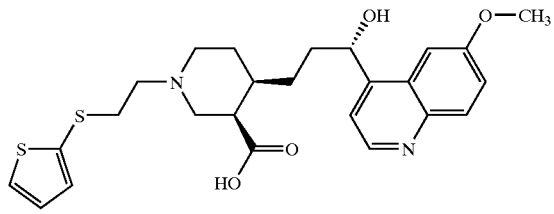

2. Description of the Art (3R,4R)-4-[3-Hydroxy-3-(6-methoxyquinolin-4-yl)propyl]-1-[2-(2-thienylthio)ethyl]-piperidine-3-carboxylic acid and its preparation has been disclosed in U.S. Pat. No. 6,403,610 in the form of its 2 diastereoisomers, known as diastereoisomer A and diastereoisomer B. In U.S. Pat. No. 6,403,610, the disclosure of which is hereby incorporated by reference, the diastereoisomers obtained existed in the amorphous form. Among the diastereoisomers of this quinolylpropylpiperidine derivative, diastereoisomer A, (3R,4R)-4-[3-(S)-hydroxy-3-(6-methoxyquinolin-4-yl)propyl]-1-[2-(2-thienylthio)ethyl]piperidine-3-carboxylic acid, is particularly advantageous for its antibacterial activity, in particular with regard to microorganisms such as *Staphylococcus aureus, Streptococcus pneumoniae, Enterococcus faecium* or *Moraxella catharrhalis*. It is also highly advantageous because of its good activity, both by the oral route and by the injectable route, and because of its low toxicity.

SUMMARY OF THE INVENTION

The present invention comprises crystalline forms of 3R,4R)-4-[3-(S)-hydroxy-3-(6-methoxyquinolin-4-yl)propyl]-1-[2-(2-thienylthio)ethyl]piperidine-3-carboxylic acid, represented by the structure:

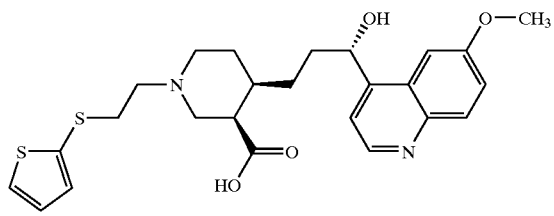

and as characterized herein by powder X-ray diffraction patterns as form A and form B, processes for preparing form A of (3R,4R)-4-[3-(S)-hydroxy-3-(6-methoxyquinolin-4-yl)propyl]-1-[2-(2-thienylthio)ethyl]piperidine-3-carboxylic acid from the purified amorphous form of (3R,4R)-4-[3-(S)-hydroxy-3-(6-methoxyquinolin-4-yl)propyl]-1-[2-(2-thienylthio)ethyl]piperidine-3-carboxylic acid, a processes for preparing form A of (3R,4R)-4-[3-(S)-hydroxy-3-(6-methoxyquinolin-4-yl)propyl]-1-[2-(2-thienylthio)ethyl]piperidine-3-carboxylic acid by heating monohydrated form C of (3R,4R)-4-[3-(S)-hydroxy-3-(6-methoxyquinolin-4-yl)propyl]-1-[2-(2-thienylthio)ethyl]piperidine-3-carboxylic acid at a temperature from about 148° C. to about 153° C., a pharmaceutical composition comprising form A of (3R,4R)-4-[3-(S)-hydroxy-3-(6-methoxyquinolin-4-yl)propyl]-1-[2-(2-thienylthio)ethyl]piperidine-3-carboxylic acid, a pharmaceutical composition comprising form A of (3R,4R)-4-[3-(S)-hydroxy-3-(6-methoxyquinolin-4-yl)propyl]-1-[2-(2-thienylthio)ethyl]piperidine-3-carboxylic acid and form B of (3R,4R)-4-[3-(S)-hydroxy-3-(6-methoxyquinolin-4-yl)propyl]-1-[2-(2-thienylthio)ethyl]piperidine-3-carboxylic acid or monohydrated form C of (3R,4R)-4-[3-(S)-hydroxy-3-(6-methoxyquinolin-4-yl)propyl]-1-[2-(2-thienylthio)ethyl]piperidine-3-carboxylic acid, a pharmaceutical composition comprising form A of (3R,4R)-4-[3-(S)-hydroxy-3-(6-methoxyquinolin-4-yl)propyl]-1-[2-(2-thienylthio)ethyl]piperidine-3-carboxylic acid, form B of (3R,4R)-4-[3-(S)-hydroxy-3-(6-methoxyquinolin-4-yl)propyl]-1-[2-(2-thienylthio)ethyl]piperidine-3-carboxylic acid and monohydrated form C of (3R,4R)-4-[3-(S)-hydroxy-3-(6-methoxyquinolin-4-yl)propyl]-1-[2-(2-thienylthio)ethyl]piperidine-3-carboxylic acid, a method for treating a bacterial infection with form A of (3R,4R)-4-[3-(S)-hydroxy-3-(6-methoxyquinolin-4-yl)propyl]-1-[2-(2-thienylthio)ethyl]piperidine-3-carboxylic acid, a method for treating a bacterial infection with form A of (3R,4R)-4-[3-(S)-hydroxy-3-(6-methoxyquinolin-4-yl)propyl]-1-[2-(2-thienylthio)ethyl]piperidine-3-carboxylic acid and form B of (3R,4R)-4-[3-(S)-hydroxy-3-(6-methoxyquinolin-4-yl)propyl]-1-[2-(2-thienylthio)ethyl]piperidine-3-carboxylic acid or monohydrated form C of (3R,4R)-4-[3-(S)-hydroxy-3-(6-methoxyquinolin-4-yl)propyl]-1-[2-(2-thienylthio)ethyl]piperidine-3-carboxylic acid, and a method for treating a bacterial infection with form A of (3R,4R)-4-[3-(S)-hydroxy-3-(6-methoxyquinolin-4-yl)propyl]-1-[2-(2-thienylthio)ethyl]piperidine-3-carboxylic acid, form B of (3R,4R)-4-[3-(S)-hydroxy-3-(6-methoxyquinolin-4-yl)propyl]-1-[2-(2-thienylthio)ethyl]piperidine-3-carboxylic acid and monohydrated form C of (3R,4R)-4-[3-(S)-hydroxy-3-(6-methoxyquinolin-4-yl)propyl]-1-[2-(2-thienylthio)ethyl]piperidine-3-carboxylic acid.

A broad embodiment of this invention is directed to crystalline forms of (3R,4R)-4-[3-(S)-hydroxy-3-(6-methoxyquinolin-4-yl)propyl]-1-[2-(2-thienylthio)ethyl]-piperidine-3-carboxylic acid, characterized herein by powder X-ray diffraction pattern data as form A and form B.

One embodiment of this invention is directed to a process for the preparation of form A of (3R,4R)-4-[3-(S)-hydroxy-3-(6-methoxyquinolin-4-yl)propyl]-1-[2-(2-thienylthio)ethyl]piperidine-3-carboxylic acid comprising preparing a solution of purified amorphous (3R,4R)-4-[3-(S)-hydroxy-3-(6-methoxyquinolin-4-yl)propyl]-1-[2-(2-thienylthio)ethyl]piperidine-3-carboxylic acid in acetonitrile by heating to reflux, cooling the solution to 20° C. to 25° C. over a suitable period of time, isolating the crystals by filtration and optionally drying said crystals.

Another embodiment of this invention is directed to a process for the preparation of form A of (3R,4R)-4-[3-(S)-hydroxy-3-(6-methoxyquinolin-4-yl)propyl]-1-[2-(2-thienylthio)ethyl]piperidine-3-carboxylic acid comprising preparing a saturated solution of purified amorphous (3R,4R)-4-[3-(S)-hydroxy-3-(6-methoxyquinolin-4-yl)propyl]-1-[2-(2-thienylthio)ethyl]piperidine-3-carboxylic acid in a suitable solvent, and evaporating the saturated solution at 20° C. to 25° C. and at atmospheric pressure over a suitable period of time.

A further embodiment of this invention is directed to a process for the preparation of form A of (3R,4R)-4-[3-(S)-hydroxy-3-(6-methoxyquinolin-4-yl)propyl]-1-[2-(2-thienylthio)ethyl]piperidine-3-carboxylic acid comprising the step of heating monohydrated form C of (3R,4R)-4-[3-(S)-hydroxy-3-(6-methoxyquinolin-4-yl)propyl]-1-[2-(2-thienylthio)ethyl]piperidine-3-carboxylic acid at a temperature from about 148° C. to about 153° C.

Another embodiment of this invention is directed to a pharmaceutical composition comprising form A of (3R,4R)-4-[3-(S)-hydroxy-3-(6-methoxyquinolin-4-yl)propyl]-1-[2-(2-thienylthio)ethyl]piperidine-3-carboxylic acid and one or more pharmaceutically acceptable adjuvants or diluents.

A further embodiment of this invention is directed to a pharmaceutical composition comprising form A of (3R,4R)-4-[3-(S)-hydroxy-3-(6-methoxyquinolin-4-yl)propyl]-1-[2-(2-thienylthio)ethyl]piperidine-3-carboxylic acid and form B of (3R,4R)-4-[3-(S)-hydroxy-3-(6-methoxyquinolin-4-yl)propyl]-1-[2-(2-thienylthio)ethyl]piperidine-3-carboxylic acid or monohydrated form C of (3R,4R)-4-[3-(S)-hydroxy-3-(6-methoxyquinolin-4-yl)propyl]-1-[2-(2-thienylthio)ethyl]piperidine-3-carboxylic acid and one or more pharmaceutically acceptable adjuvants or diluents.

A further embodiment of this invention is directed to a pharmaceutical composition comprising form A of (3R,4R)-4-[3-(S)-hydroxy-3-(6-methoxyquinolin-4-yl)propyl]-1-[2-(2-thienylthio)ethyl]piperidine-3-carboxylic acid and form B of (3R,4R)-4-[3-(S)-hydroxy-3-(6-methoxyquinolin-4-yl)propyl]-1-[2-(2-thienylthio)ethyl]piperidine-3-carboxylic acid and monohydrated form C of (3R,4R)-4-[3-(S)-hydroxy-3-(6-methoxyquinolin-4-yl)propyl]-1-[2-(2-thienylthio)ethyl]piperidine-3-carboxylic acid and one or more pharmaceutically acceptable adjuvants or diluents.

Another embodiment of this invention is directed to a method for treating a bacterial infection comprising administering to a patient in need of such treatment a therapeutically effective amount of form A of (3R,4R)-4-[3-(S)-hydroxy-3-(6-methoxyquinolin-4-yl)propyl]-1-[2-(2-thienylthio)ethyl]piperidine-3-carboxylic acid.

A further embodiment of this invention is directed to a method for treating a bacterial infection comprising administering to a patient in need of such treatment a therapeutically effective amount of form A of 3R,4R)-4-[3-(S)-hydroxy-3-(6-methoxyquinolin-4-yl)propyl]-1-[2-(2-thienylthio)ethyl]piperidine-3-carboxylic acid and form B of 3R,4R)-4-[3-(S)-hydroxy-3-(6 -methoxyquinolin-4-yl)propyl]-1-[2-(2-thienylthio)ethyl]piperidine-3-carboxylic acid or monohydrated form C of 3R,4R)-4-[3-(S)-hydroxy-3-(6-methoxyquinolin-4-yl)propyl]-1-[2-(2-thienylthio)ethyl]piperidine-3-carboxylic acid.

Another embodiment of this invention is directed to a method for treating a bacterial infection comprising administering to a patient in need of said treatment a therapeutically effective amount of form A of 3R,4R)-4-[3-(S)-hydroxy-3-(6-methoxyquinolin-4-yl)propyl]-1-[2-(2-thienylthio)ethyl]piperidine-3-carboxylic acid, form B of 3R,4R)-4-[3-(S)-hydroxy-3-(6-methoxyquinolin-4-yl)propyl]-1-[2-(2-thienylthio)ethyl]piperidine-3-carboxylic acid and monohydrated form C of 3R,4R)-4-[3-(S)-hydroxy-3-(6-methoxyquinolin-4-yl)propyl]-1-[2-(2-thienylthio)ethyl]piperidine-3-carboxylic acid.

DETAILED DESCRIPTION OF THE INVENTION

The crystalline form of (3R,4R)-4-[3-(S)-hydroxy-3-(6-methoxyquinolin-4-yl)propyl]-1-[2-(2-thienylthio)ethyl]piperidine-3-carboxylic acid, according to the invention, hereinafter known as form A, exists in the form of a white to pale-yellow crystalline powder; it melts at approximately 166° C. and it has been defined by the indexing of its powder X-ray diffraction pattern described hereinbelow.

Form A of (3R,4R)-4-[3-(S)-hydroxy-3-(6-methoxyquinolin-4-yl)propyl]-1-[2-(2-thienylthio)ethyl]piperidine-3-carboxylic acid can be prepared by crystallization by evaporation of a saturated solution of the, preferably purified, amorphous product by:

dissolution in acetonitrile, by heating to the reflux temperature and then cooling to a temperature of 20° C.–25° C., over a period of time of at least one and one-half hours;

dissolution and maintenance at a temperature of 20° C.–25° C. and at atmospheric pressure, after a period of a few days to about 30 days, in acetone, methyl ethyl ketone, methyl isobutyl ketone, chloroform, dichloromethane, dimethyl sulfoxide, methanol, ethanol, 2-propanol, 2-methylpropanol, n-heptane, toluene, diisopropyl ether, methyl t-butyl ether or tetrahydrofuran (maturing for 5 to 30 days).

The purified amorphous form is prepared beforehand by chiral HPLC, as disclosed previously in U.S. Pat. No. 6,403,610.

According to the invention, form A of (3R,4R)-4-[3-(S)-hydroxy-3-(6-methoxyquinolin-4-yl)propyl]-1-[2-(2-thienylthio)ethyl]piperidine-3-carboxylic acid can also be prepared by crystallization of the crude amorphous product from absolute ethanol or methanol, treating with active charcoal and filtering while hot, and then initiating crystallization at 51° C. with 1.5% to 1.7% of crystals of form A and cooling to a temperature of about 20° C.

The crude amorphous form is prepared beforehand as described previously in U.S. Pat. No. 6,403,610.

According to another aspect of the present invention, form A can also be obtained from another monohydrate crystalline form known hereinbelow as form C. Below 50% humidity and between 20° C. and 80° C., form C undergoes a loss in mass of 3.7% by weight (1 mole of water/mole of the acid). This loss in mass corresponds to dehydration of form C to give another form of (3R,4R)-4-[3-(S)-hydroxy-3-(6-methoxyquinolin-4-yl)propyl]-1-[2-(2-thienylthio)ethyl]piperidine-3-carboxylic acid, known hereinbelow as form B. Form B is anhydrous, and exhibits melting beginning at 147.6° C.–148° C. and then changes to form A at about 153° C. Form B is obtained more particularly by heating form C to 70° C. or from form C held at 25° C. at 0% humidity.

Form C of (3R,4R)-4-[3-(S)-hydroxy-3-(6-methoxyquinolin-4-yl)propyl]-1-[2-(2-thienylthio)ethyl]piperidine-3-carboxylic acid can be obtained by crystallization from mixtures of water and water-miscible organic solvents, in particular under the conditions hereinbelow:

by evaporation at 20° C.–25° C., for a period of time ranging up to 7 days to 9 days, of a saturated solution of the amorphous form in a methyl ethyl ketone/ demineralized water (50/50 by volume) mixture or in a methanol or ethanol/demineralized water (50/50 by volume) mixture;

by stirring a suspension of form A at a temperature of 20° C.–25° C., in tetrahydrofuran/demineralized water (50/50 by volume), methyl ethyl ketone/demineralized water (80/20 by volume to 20/80 by volume), acetonitrile/demineralized water (50/50 by volume to 20/80 by volume) or ethanol or methanol/demineralized water (50/50 by volume) mixtures, for 5 to about 30 days.

Form B of (3R,4R)-4-[3-(S)-hydroxy-3-(6-methoxyquinolin-4-yl)propyl]-1-[2-(2-thienylthio)ethyl]piperidine-3-carboxylic acid can be obtained either, on the one hand, by dehydration of form C or, on the other hand, by slow evaporation, at 20° C.–25° C. while flushing with nitrogen, of a solution of the amorphous product in toluene or by evaporation of a saturated solution of the amorphous product in dimethylformamide, at 40° C., under reduced pressure for approximately 16 hours. Form B can be used as an intermediate for the preparation of form A. Form B is an anhydrous form and is also defined hereinbelow by the indexing of its powder X-ray diffraction pattern diagram.

Powder X-Ray Diffraction

The analyses are carried out on a Bruker D8 diffractometer having a copper-anticathode tube equipped with a front monochromator (wavelength of the copper $K\alpha_1$ line: 1.54060 Å). The arrangement is of Bragg-Brentano type, with a point scintillation detector. The angular range swept extends from 2 to 40 degrees $2\theta$ with a step of 0.02 degrees $2\theta$. The counting time is 120 seconds per step.

Form A

Form A crystallizes in a monoclinic lattice (space group $P2_1$, Z=2), the unit cell parameters of which are:

$a$=14.936 Å $\alpha$=90°

$b$=7.604 Å $\beta$=104.079°

$c$=11.315 Å $\gamma$=90° $V$=1248.2 Å$^3$

The complete indexing of the lines of the powder X-ray diffraction pattern of form A of (3R,4R)-4-[3-(S)-hydroxy-3-(6-methoxyquinolin-4-yl)propyl]-1-[2-(2-thienylthio)ethyl] piperidine-3-carboxylic acid at T=295 K, in lattice spacing and in "mean $\lambda_{Cu\ K\alpha}$" $2\theta$ positions, gives the following result:

| h | k | l | Multiplicity factor J | Lattice spacing (Å) | $2\theta$ "mean $\lambda_{Cu\ K\alpha}$" 1.54184 Å |
|---|---|---|---|---|---|
| 1 | 0 | 0 | 2 | 14.4954 | 6.0971 |
| 0 | 0 | 1 | 2 | 10.9797 | 8.0523 |
| -1 | 0 | 1 | 2 | 10.0030 | 8.8400 |
| 1 | 0 | 1 | 2 | 7.8775 | 11.2320 |
| 2 | 0 | 0 | 2 | 7.2477 | 12.2116 |
| -2 | 0 | 1 | 2 | 6.8662 | 12.8930 |
| 1 | 1 | 0 | 4 | 6.7356 | 13.1440 |
| 0 | 1 | 1 | 4 | 6.2527 | 14.1640 |
| -1 | 1 | 1 | 4 | 6.0549 | 14.6294 |
| -1 | 0 | 2 | 2 | 5.6060 | 15.8078 |
| 0 | 0 | 2 | 2 | 5.4898 | 16.1447 |
| 1 | 1 | 1 | 4 | 5.4720 | 16.1977 |
| 2 | 0 | 1 | 2 | 5.4674 | 16.2112 |
| 2 | 1 | 0 | 4 | 5.2472 | 16.8964 |
| -2 | 1 | 1 | 4 | 5.0969 | 17.3987 |
| -2 | 0 | 2 | 2 | 5.0015 | 17.7331 |
| -3 | 0 | 1 | 2 | 4.8826 | 18.1687 |
| 3 | 0 | 0 | 2 | 4.8318 | 18.3612 |
| 1 | 0 | 2 | 2 | 4.7641 | 18.6246 |
| -1 | 1 | 2 | 4 | 4.5129 | 19.6713 |
| 0 | 1 | 2 | 4 | 4.4516 | 19.9449 |
| 2 | 1 | 1 | 4 | 4.4396 | 19.9992 |
| -2 | 1 | 2 | 4 | 4.1791 | 21.2601 |
| -3 | 0 | 2 | 2 | 4.1648 | 21.3338 |
| -3 | 1 | 1 | 4 | 4.1089 | 21.6273 |
| 3 | 1 | 0 | 4 | 4.0786 | 21.7904 |
| 3 | 0 | 1 | 2 | 4.0720 | 21.8259 |
| 1 | 1 | 2 | 4 | 4.0376 | 22.0144 |
| 2 | 0 | 2 | 2 | 3.9388 | 22.5737 |

Form B

Form B can be used as intermediate for the preparation of the form A. Form B exhibits the following characteristics at 295 K:

orthorhombic unit cell (space group $P2_12_12_1$, Z=4)

$a$=19.3231 Å $\alpha$=$\beta$=$\gamma$=90°

$b$=12.9456 Å

$c$=10.0251 Å $V$=2507.79 Å$^3$

The asymmetric unit cell is composed of a molecule of (3R,4R)-4-[3-(S)-hydroxy-3-(6-methoxyquinolin-4-yl)propyl]-1-[2-(2-thienylthio)ethyl]piperidine-3-carboxylic acid. It is a pure form.

The complete indexing of the lines of the powder X-ray diffraction pattern of form B is described below:

| h | k | l | Multiplicity factor J | Lattice sacing (Å) | $2\theta$ "mean $\lambda_{Cu\ K\alpha}$" 1.54184 Å |
|---|---|---|---|---|---|
| 1 | 1 | 0 | 4 | 10.7550 | 8.2207 |
| 2 | 0 | 0 | 2 | 9.6616 | 9.1530 |
| 1 | 0 | 1 | 4 | 8.8988 | 9.9395 |
| 0 | 1 | 1 | 4 | 7.9263 | 11.1627 |
| 2 | 1 | 0 | 4 | 7.7429 | 11.4279 |
| 1 | 1 | 1 | 8 | 7.3333 | 12.0685 |
| 2 | 0 | 1 | 4 | 6.9567 | 12.7244 |
| 0 | 2 | 0 | 2 | 6.4728 | 13.6801 |
| 1 | 2 | 0 | 4 | 6.1376 | 14.4311 |
| 2 | 1 | 1 | 8 | 6.1280 | 14.4540 |
| 3 | 1 | 0 | 4 | 5.7667 | 15.3648 |
| 0 | 2 | 1 | 4 | 5.4378 | 16.3001 |
| 3 | 0 | 1 | 4 | 5.4190 | 16.3573 |
| 2 | 2 | 0 | 4 | 5.3775 | 16.4842 |
| 1 | 2 | 1 | 8 | 5.2345 | 16.9378 |
| 0 | 0 | 2 | 2 | 5.0125 | 17.6937 |
| 3 | 1 | 1 | 8 | 4.9987 | 17.7432 |
| 1 | 0 | 2 | 4 | 4.8520 | 18.2843 |
| 4 | 0 | 0 | 2 | 4.8308 | 18.3652 |
| 2 | 2 | 1 | 8 | 4.7388 | 18.7247 |
| 0 | 1 | 2 | 4 | 4.6744 | 18.9852 |
| 3 | 2 | 0 | 4 | 4.5657 | 19.4415 |
| 1 | 1 | 2 | 8 | 4.5433 | 19.5381 |
| 4 | 1 | 0 | 4 | 4.5259 | 19.6140 |
| 2 | 0 | 2 | 4 | 4.4494 | 19.9549 |
| 4 | 0 | 1 | 4 | 4.3519 | 20.4067 |

Form A of (3R,4R)-4-[3-(S)-hydroxy-3-(6-methoxyquinolin-4-yl)propyl]-1-[2-(2-thienylthio)ethyl]piperidine-3-carboxylic acid is anhydrous and is not hygroscopic; it is stable between 0% and 100% relative humidity. After storage at 97% relative humidity for 11 weeks at 20° C., form A is still anhydrous and stable. This crystalline form also exhibits the advantage of being stable at high temperature, namely up to its melting point.

Form A of (3R,4R)-4-[3-(S)-hydroxy-3-(6-methoxyquinolin-4-yl)propyl]-1-[2-(2-thienylthio)ethyl]piperidine-3-carboxylic acid exhibits the advantage of an improved degree of purity and thus makes possible the preparation of pharmaceutical compositions not exhibiting an amount of impurities which are undesirable in nature or in degree.

In particular, the microanalytical results obtained for the amorphous form disclosed in U.S. Pat. No. 6,403,610, compared with the results obtained for the batch of form A described in example 1, demonstrate this improvement in the purity:

|  |  | C % | H % | N % | O % | S % |
|---|---|---|---|---|---|---|
| U.S. Pat. No. 6,403,610, example 33, diastereoisomer A - amorphous product | Measured | 61.76 | 6.30 | 5.87 | — | 12.32 |
|  |  | 61.30 | 6.38 | 5.85 | — | 12.38 |
| Example 1 - form A | Measured | 61.56 | 6.66 | 5.69 | — | 13.05 |
|  | Calculated | 61.70 | 6.21 | 5.76 | 13.15 | 13.18 |

Furthermore, the optical rotations testify to this improvement in purity:

|  | $\alpha^{20}_D$ dichloromethane at 0.5% |
|---|---|
| U.S. Pat. No. 6,403,610, example 33, diastereoisomer A - amorphous product | −73.8° ± −1.4° |
| Example 1 - form A | −77.8° ± −1.3° |

The present invention also relates to the pharmaceutical compositions comprising form A of (3R,4R)-4-[3-(S)-hydroxy-3-(6-methoxyquinolin-4-yl)propyl]-1-[2-(2-thienylthio)ethyl]piperidine-3-carboxylic acid according to the invention, in the pure state or optionally in combination with one and/or other crystalline forms B or C and/or in the form of a combination with one or more compatible and pharmaceutically acceptable diluents or adjuvants.

The compositions according to the invention can be used orally, parenterally, topically or rectally or as aerosols.

Tablets, pills, gelatin capsules, powders or granules can be used as solid compositions for oral administration. In these compositions, form A according to the invention is mixed with one or more inert diluents or adjuvants, such as sucrose, lactose or starch. These compositions can comprise substances other than diluents, for example a lubricant, such as magnesium stearate, or a coating intended for controlled release.

Form A can also be used for the preparation of liquid compositions for oral administration; use may be made of pharmaceutically acceptable solutions, suspensions, emulsions, syrups and elixirs comprising inert diluents, such as water or liquid paraffin. These compositions can also comprise substances other than diluents, for example wetting, sweetening or flavoring agents.

Form A can also be used for the preparation of compositions for parenteral administration. These compositions can be emulsions or sterile solutions. Use may be made, as solvent or vehicle, of water, propylene glycol, a polyethylene glycol, vegetable oils, in particular olive oil, or injectable organic esters, for example ethyl oleate. These compositions can also comprise adjuvants, in particular wetting, isotonizing, emulsifying, dispersing and stabilizing agents.

Sterilization can be carried out in several ways, for example using a bacteriological filter, by irradiation or by heating. Compositions for parenteral administration can also be prepared in the form of sterile solid compositions which can be dissolved at the time of use in sterile water or any other injectable sterile medium.

Compositions for rectal administration include suppositories or rectal capsules which comprise, in addition to the active principle, excipients such as cocoa butter, semisynthetic glycerides or polyethylene glycols.

Compositions for topical administration can, for example, be creams, ointments, lotions or aerosols.

Compositions for inhalation can in particular be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, form A of (3R,4R)-4-[3-(S)-hydroxy-3-(6-methoxyquinolin-4-yl)propyl]-1-[2-(2-thienylthio)ethyl]-piperidine-3-carboxylic acid is finely divided and combined with a water-soluble solid diluent or vehicle with a particle size of 30 μm to 80 μm, for example dextran, mannitol or lactose.

As a whole, all these compositions exhibit the advantage of a high degree of purity of active principle.

EXAMPLES

The following examples, given without implied limitation, illustrate the present invention.

Example 1

Form A of (3R,4R)-4-[3-(S)-hydroxy-3-(6-methoxyquinolin-4-yl)propyl]-1-[2-(2-thienylthio)-ethyl] piperidine-3-carboxylic acid A solution of (3R,4R)-4-[3-(R,S)-hydroxy-3-(6-methoxyquinolin-4-yl)propyl]-1-[2--thienylthio)ethyl]piperidine-3-carboxylic acid in dichloromethane is chromatographed on a column with a length of 35 cm and a diameter of 8 cm packed with 1200 g of Kromasil® silica (particle size of 10μ/m). A precolumn with a length of 10 cm and a diameter of 6 cm comprising 250 g of Merck silica (particle size 15–25 μm) is added to the system. Elution is carried out using a dichloromethane/methanol/acetonitrile (60/20/20 by volume) mixture. The flow rate is adjusted from 150 cm³/min to 180 cm³/min and detection is carried out in the ultraviolet at 280 nm. This operation, repeated three times, to treat a batch of 20 g, results in two diastereoisomers being obtained. The intermediate fractions are concentrated and reinjected into the column. The fractions corresponding to the first diastereoisomer (diastereoisomer A) are concentrated to dryness under reduced pressure (5 kPa) at a temperature of about 40° C., and the residue is crystallized after dissolving in 60 cm³ acetonitrile, bringing to reflux for 5 minutes and then cooling to a temperature of 20° C. over 1 hour 30 minutes. The crystals are filtered off and washed twice with 20 cm³ of acetonitrile and then twice with 20 cm³ of ethyl ether. After drying in an oven under reduced pressure (13 Pa) at a temperature of about 40° C., diastereoisomer A of (3R,4R)-4-[3-(S)-hydroxy-3-(6-methoxyquinolin-4-yl)propyl]-1-[2-(2-thienylthio)ethyl]piperidine-3-carboxylic acid, (5.38 g) is obtained in the form of white crystals (form A).

Optical rotation $[\alpha]_D^{20}=-77.8°$ (in dichloromethane at 0.5%).

Example 2

Monohydrated form C of (3R,4R)-4-[3-(S)-hydroxy-3-(6-methoxyquinolin-4-yl)propyl]-1-[2-(2-thienylthio)ethyl]piperidine-3-carboxylic acid A suspension of about 460 mg of (3R,4R)-4-[3-(S)-hydroxy-3-(6-methoxyquinolin-4-yl)propyl]-1-[2-(2-thienylthio)ethyl]piperidine-3-carboxylic acid in 1.84 cm³ of a water/methanol (50/50) mixture is brought to reflux until completely dissolved. The solution is cooled to approximately 20° C. The crystals which appear during the cooling are filtered off and then dried at about 20° C. and normal pressure. Form C of (3R,4R)-4-[3-(S)-hydroxy-3-(6-methoxyquinolin-4-yl)propyl]-1-[2-(2-thienylthio)ethyl]piperidine-3-carboxylic acid (436.3 mg) is obtained in the form of white crystals.

Form A of (3R,4R)-4-[3-(S)-hydroxy-3-(6-methoxyquinolin-4-yl)propyl]-1-[2-(2-thienylthio)ethyl]piperidine-3-carboxylic acid can be obtained by dehydration of form C under the conditions described above.

What is claimed is:

1. A crystalline form A of (3R,4R)-4-[3-(S)-hydroxy-3-(6-methoxyquinolin-4-yl)propyl]-1-[2-(2-thienylthio)ethyl]piperidine-3-carboxylic acid having a powder X-ray diffraction pattern

| h | k | l | Multiplicity factor J | Lattice spacing (Å) | 2θ "mean $\lambda_{Cu\,K\alpha}$" 1.54184 Å |
|---|---|---|---|---|---|
| 1 | 0 | 0 | 2 | 14.4954 | 6.0971 |
| 0 | 0 | 1 | 2 | 10.9797 | 8.0523 |
| −1 | 0 | 1 | 2 | 10.0030 | 8.8400 |
| 1 | 0 | 1 | 2 | 7.8775 | 11.2320 |
| 2 | 0 | 0 | 2 | 7.2477 | 12.2116 |
| −2 | 0 | 1 | 2 | 6.8662 | 12.8930 |
| 1 | 1 | 0 | 4 | 6.7356 | 13.1440 |
| 0 | 1 | 1 | 4 | 6.2527 | 14.1640 |
| −1 | 1 | 1 | 4 | 6.0549 | 14.6294 |
| −1 | 0 | 2 | 2 | 5.6060 | 15.8078 |
| 0 | 0 | 2 | 2 | 5.4898 | 16.1447 |
| 1 | 1 | 1 | 4 | 5.4720 | 16.1977 |
| 2 | 0 | 1 | 2 | 5.4674 | 16.2112 |
| 2 | 1 | 0 | 4 | 5.2472 | 16.8964 |
| −2 | 1 | 1 | 4 | 5.0969 | 17.3987 |
| −2 | 0 | 2 | 2 | 5.0015 | 17.7331 |
| −3 | 0 | 1 | 2 | 4.8826 | 18.1687 |
| 3 | 0 | 0 | 2 | 4.8318 | 18.3612 |
| 1 | 0 | 2 | 2 | 4.7641 | 18.6246 |
| −1 | 1 | 2 | 4 | 4.5129 | 19.6713 |
| 0 | 1 | 2 | 4 | 4.4516 | 19.9449 |
| 2 | 1 | 1 | 4 | 4.4396 | 19.9992 |
| −2 | 1 | 2 | 4 | 4.1791 | 21.2601 |
| −3 | 0 | 2 | 2 | 4.1648 | 21.3338 |
| −3 | 1 | 1 | 4 | 4.1089 | 21.6273 |
| 3 | 1 | 0 | 4 | 4.0786 | 21.7904 |
| 3 | 0 | 1 | 2 | 4.0720 | 21.8259 |
| 1 | 1 | 2 | 4 | 4.0376 | 22.0144 |
| 2 | 0 | 2 | 2 | 3.9388 | 22.5737 | at 295 K expressed in terms of h, k, l, multiplicity factor J, lattice spacing in Å and 2θ.

2. A crystalline form A of (3R,4R)-4-[3-(S)-hydroxy-3-(6-methoxyquinolin-4-yl)propyl]-1-[2-(2-ethyl]piperidine-3-carboxylic acid according to claim 1 wherein said form A crystalizes in a monoclinic lattice (space group P2₁, Z=2) and wherein the unit cell parameters are:

$a$=4.936 Å $\alpha$=90°

$b$=7.604 Å $\beta$=104.079°

$c$=11.315 Å $\gamma$=90° $V$=1248.2 Å³ at 295 K.

3. A crystalline form B of (3R,4R)-4-[3-(S)-hydroxy-3-(6-methoxyquinolin-4-yl)propyl]-1-[2-(2-thienylthio)ethyl] piperidine-3-carboxylic acid having a powder X-ray diffraction pattern

| h | k | l | Multiplicity factor J | Lattice spacing (Å) | 2θ "mean $\lambda_{Cu\,K\alpha}$" 1.54184 Å |
|---|---|---|---|---|---|
| 1 | 1 | 0 | 4 | 10.7550 | 8.2207 |
| 2 | 0 | 0 | 2 | 9.6616 | 9.1530 |
| 1 | 0 | 1 | 4 | 8.8988 | 9.9395 |
| 0 | 1 | 1 | 4 | 7.9263 | 11.1627 |
| 2 | 1 | 0 | 4 | 7.7429 | 11.4279 |
| 1 | 1 | 1 | 8 | 7.3333 | 12.0685 |
| 2 | 0 | 1 | 4 | 6.9567 | 12.7244 |
| 0 | 2 | 0 | 2 | 6.4728 | 13.6801 |
| 1 | 2 | 0 | 4 | 6.1376 | 14.4311 |
| 2 | 1 | 1 | 8 | 6.1280 | 14.4540 |
| 3 | 1 | 0 | 4 | 5.7667 | 15.3648 |
| 0 | 2 | 1 | 4 | 5.4378 | 16.3001 |
| 3 | 0 | 1 | 4 | 5.4190 | 16.3573 |
| 2 | 2 | 0 | 4 | 5.3775 | 16.4842 |
| 1 | 2 | 1 | 8 | 5.2345 | 16.9378 |
| 0 | 0 | 2 | 2 | 5.0125 | 17.6937 |
| 3 | 1 | 1 | 8 | 4.9987 | 17.7432 |
| 1 | 0 | 2 | 4 | 4.8520 | 18.2843 |
| 4 | 0 | 0 | 2 | 4.8308 | 18.3652 |
| 2 | 2 | 1 | 8 | 4.7388 | 18.7247 |
| 0 | 1 | 2 | 4 | 4.6744 | 18.9852 |
| 3 | 2 | 0 | 4 | 4.5657 | 19.4415 |
| 1 | 1 | 2 | 8 | 4.5433 | 19.5381 |
| 4 | 1 | 0 | 4 | 4.5259 | 19.6140 |
| 2 | 0 | 2 | 4 | 4.4494 | 19.9549 |
| 4 | 0 | 1 | 4 | 4.3519 | 20.4067 | at 295 K expressed in terms of h, k, l, multiplicity factor J, lattice spacing in Å and 2θ.

4. A crystalline form B of (3R,4R)-4-[3-(S)-hydroxy-3-(6-methoxyquinolin-4-yl)propyl]-1-[2-(2-thienylthio)ethyl] piperidine-3-carboxylic acid according to claim 3 wherein the unit cell is orthorhombic (space group P2₁2₁2₁, Z=4) and wherein the unit cell parameters are:

$a$=19.3231 Å $\alpha$=$\beta$=$\gamma$=9°

$b$=12.9456 Å

$c$=10.0251 Å $V$=2507.79 Å³ at 295 K.

* * * * *